US010501704B2

(12) United States Patent
Breivik et al.

(10) Patent No.: US 10,501,704 B2
(45) Date of Patent: Dec. 10, 2019

(54) VERY LONG CHAIN POLYUNSATURATED FATTY ACIDS FROM NATURAL OILS

(71) Applicant: Epax Norway AS, Ålesund (NO)

(72) Inventors: Harald Breivik, Inndyr (NO); Harald Svensen, Ålesund (NO)

(73) Assignee: EPAX NORWAY AS, Ãlesund (NO)

( * ) Notice: Subject to any disclaimer, the term of this patent is extended or adjusted under 35 U.S.C. 154(b) by 0 days.

(21) Appl. No.: 15/570,411

(22) PCT Filed: May 12, 2016

(86) PCT No.: PCT/NO2016/050088
§ 371 (c)(1),
(2) Date: Oct. 30, 2017

(87) PCT Pub. No.: WO2016/182452
PCT Pub. Date: Nov. 17, 2016

(65) Prior Publication Data
US 2018/0163156 A1 Jun. 14, 2018

Related U.S. Application Data

(60) Provisional application No. 62/160,690, filed on May 13, 2015.

(51) Int. Cl.
C11B 3/00 (2006.01)
C11C 1/04 (2006.01)
A61K 31/202 (2006.01)
C11B 3/12 (2006.01)
C11B 7/00 (2006.01)
C11C 1/02 (2006.01)
C11C 1/08 (2006.01)
C11C 1/10 (2006.01)
C11C 3/00 (2006.01)
C11C 3/02 (2006.01)
C11C 1/00 (2006.01)
C11B 3/04 (2006.01)
C11B 3/06 (2006.01)

(52) U.S. Cl.
CPC ......... C11B 3/006 (2013.01); A61K 31/202 (2013.01); C11B 3/001 (2013.01); C11B 3/12 (2013.01); C11B 7/0058 (2013.01); C11C 1/002 (2013.01); C11C 1/025 (2013.01); C11C 1/04 (2013.01); C11C 1/08 (2013.01); C11C 1/10 (2013.01); C11C 1/103 (2013.01); C11C 3/003 (2013.01); C11C 3/02 (2013.01); C11B 3/04 (2013.01); C11B 3/06 (2013.01)

(58) Field of Classification Search
CPC ......... C07C 57/02; C07C 57/03; C11B 3/006; C11B 3/001; C11B 3/04; C11B 3/06; C11B 3/12; C11B 7/0058; C11C 1/002; C11C 1/025; C11C 1/04; C11C 1/08
See application file for complete search history.

(56) References Cited

U.S. PATENT DOCUMENTS

| 2,347,565 | A |   | 4/1944  | Kokatnur |
|-----------|---|---|---------|----------|
| 4,377,526 | A | * | 3/1983  | Fujita ................ C07C 51/42 554/185 |
| 4,792,418 | A | * | 12/1988 | Rubin ................. C09F 5/02 435/134 |
| 6,537,787 | B1| * | 3/2003  | Breton ................ C11C 1/045 435/134 |
| 2006/0134303 | A1 |   | 6/2006 | Sondbo et al. |
| 2009/0023808 | A1 | * | 1/2009 | Raman ................ A21D 2/16 514/549 |
| 2009/0203787 | A1 |   | 8/2009 | Anderson et al. |
| 2012/0083616 | A1 |   | 4/2012 | Halting Glade et al. |
| 2013/0190399 | A1 | * | 7/2013 | Raman ............... C07C 67/343 514/560 |
| 2013/0267600 | A1 |   | 10/2013 | Sepulveda Reyes et al. |
| 2013/0331588 | A1 |   | 12/2013 | Hietsch et al. |
| 2014/0100280 | A1 | * | 4/2014 | Anderson .......... C12N 9/1029 514/560 |

FOREIGN PATENT DOCUMENTS

| EP | 0 347 509 | 12/1989 |         |
|----|-----------|---------|---------|
| EP | 1 359 224 | 11/2003 |         |
| JP | 10-195023 A * | 7/1998 | ......... C07C 69/587 |
| WO | 89/11521 | 11/1989 |         |
| WO | 97/27274 | 7/1997  |         |
| WO | WO 2009/097331 A1 * | 8/2009 | ........... C12N 15/79 |

(Continued)

OTHER PUBLICATIONS

JP 10-195023A, Kanda Kenji et al., New highly unsaturated fatty acid ethyl esters, English Translation, 7 pages (Year: 1998).*

Breivik, H., et al., Production and quality control of n-3 fatty acids, 1992, Pharmakologie Clinical Pharmacology, vol. 5, pp. 25-39 Year: (1992).*

Furland, N. E., et al., Very long-chain polyunsaturated fatty acids are the major acyl groups of sphingomyelins and ceramides in the head of mammalian spermatoza, 2007, The Journal of Biological Chemistry, vol. 282, No. 25, pp. 18151-18161 (Year: 2007).*

(Continued)

Primary Examiner — Yate' K Cutliff
(74) Attorney, Agent, or Firm — Wenderoth, Lind & Ponack, L.L.P.

(57) ABSTRACT

A method of producing a composition comprising a high concentration of very long chain polyunsaturated fatty acids (VLCPUFAs) from natural oils such as fish oil, squid oil, algal oil and krill oil. In addition, a composition comprising a high concentration of very long chain polyunsaturated fatty acids isolated from such natural sources; as well as to a process for isolating separate fractions of very long chain polyunsaturated fatty acids having identical chain lengths but different degrees of unsaturation from such highly concentrated compositions is disclosed.

22 Claims, No Drawings

(56) References Cited

FOREIGN PATENT DOCUMENTS

| WO | 2010/139085 | | 12/2010 | |
|---|---|---|---|---|
| WO | 2012/088620 | | 7/2012 | |
| WO | WO 2012/112902 | * | 8/2013 | ............ A01N 37/00 |
| WO | 2019/053744 | | 3/2019 | |

OTHER PUBLICATIONS

Mansour, M. P., et al., Very-long chain (C28) highly unsaturated fatty acids in marine dinoflagellates, 1999, Phytochemistry, vol. 50, issue 4, pp. 541-548 (Year: 1999).*

Nichols, P. D., et al., Occurrence of High levels of tetracosahexaenoic acid in the jellyfish *Aureilia* sp., 2007, Lipids, vol. 38, No. 11, pp. 1207-1210 (Year: 2003).*

Rezanka, T., Analysis of Very long chain polyenoic fatty acids by high performance liquid chromatography and gas chromatography-mass spectrometry with chemical ionization, 1990, LC GC: international magazine of separation science, vol. 8, No. 7, 4 pages (Year: 1990).*

Rotstein, N. P., et al., Synthesis of very long chain (up to 36 carbon) tetra, penta and hexaenoic fatty acids in retina, 1988, Biochem , J., vol. 249, pp. 191-200 (Year: 1988).*

Van Pelt, C. K., et al., An octaene fatty acid, 4,7,10,13,16,19,22,25-octacosaoctaenoic acid (C28:8n-3), found in marine oils, 1999, Journal of Lipid Research, vol. 40, pp. 1501-1505 (Year: 1999).*

Hilditch Thomas Percy, "The Chemical Constitution of Natural Fats", 1947, 2nd ed, London: Chapman & Hall Ltd., John Wiley & Sons, Inc., New York, pp. 1-554.

J.L Guil-Guerrero et al., "Purification Process for Cod Liver Oil Polyunsaturated Fatty Acids", Journal of the American Oil Chemists' Society, 2001, vol. 78, No. 5, pp. 477-484.

Reijo Käkelä et al., "Very Long Chain Polyunsaturated Fatty Acids in the Blubber of Ringed Seals (*Phoca hispida* sp.) from Lake Saimaa, Lake Ladoga, the Baltic Sea, and Spitsbergen", Lipids, 1995, vol. 30, No. 8, pp. 725-731.

Werner Bergmann et al., "Contributions to the Study of Marine Products. XXX. Component Acids of Lipids of Sponges. I.", J. Org. Chem. 16, 1951, pp. 1206-1221.

Maged P. Mansour, "Reversed-phase high performance liquid chromatography purification of methyl esters of $C_{16}$—$C_{28}$ polyunsaurated fatty acids in microalgae, including octacosaoctaenoic acid [28:8(n-3]", Journal of Chromatography A, 2005, vol. 1097, pp. 54-58.

Karen L. Kaestle et al., "Cleavage of esters using carbonates and bicarbonates of alkali metals: synthesis of thymopentin" Tetrahedron Letters, vol. 32, Issue 3, 1991, pp. 327-330.

Ahmed M. Abu-Nasr et al., "Highly Unsaturated fatty acids. II. Fractionation by urea inclusion compounds", Journal of the American Oil Chemists Society, 1954, vol. 31, No. 1, pp. 16-20.

Carter Litchfield et al., "5,9,23-Triacontatrienoic Acid, Principle Fatty Acid of the Marine Sponge *Chondrilla nucula*", Lipids, 1980, vol. 15, No. 3, pp. 200-201.

Reino R. Linko et al., "Fatty acids of long chain length in Baltic herring lipids", Journal of the American Oil Chemists Society, 1970, vol. 47, No. 2, pp. 42-46.

Toru Ota et al., "Occurrence of All-cis-6,9,12,15,18,21-Tetracosahexaenoic Acid in Flatfish Lipids", Fisheries Science, 1994, vol. 60, No. 2, pp. 171-175.

TomášRezanka, "Very-Long Chain Fatty Acids From the Animal and Plant Kingdoms", Prog. Lipid Res., 1989, vol. 28. pp. 147-187.

Ken-ichi Kawasaki et al., "High level of 6,9,12,15,18,21-tetracosahexaenoic acid found in lipids of Ophiuroidea Ophiura sarsi Lütken", 2000, Fisheries Science, vol. 66, pp. 614-615.

Rei Suo et al., "Generation of Tetracosahexaenoic Acid in Benthic Marine Organisms", J. Oleo Sci., 2015, vol. 64. No. 7, pp. 721-727.

Mikhail V. Vysotskii et al, "Identification, isolation and characterization of tetracosapolyenoic acids in lipids of marine coelenterates" Biochimica et Biophysica Acta (BBA)—Lipids and Lipid Metabolism, 1991, vol. 1083, Issue 2, pp. 161-165.

Maged P. Mansour et al., "Lipid and fatty acid yield of nine stationary-phase microalgae: Applications and unusual $C_{24}$—$C_{28}$ polyunsaturated fatty acids", Journal of Applied Phycology, 2005, vol. 17, Issue 4, pp. 287-300.

Toru Ota et al., "Positional Distribution of 24:6(n-3) in Triacyl-sn-Glycerols from Flathead Flounder Liver and Flesh", J. Am. Oil. Chem. Soc., vol. 71, No. 5, pp. 475-478, 1994.

Toru Takagi et al., "Fatty Acids in Crinoidea and Ophiuroidea: Occurrence of All-cis-6,9,12,15,18,21-tetracosahexaenoic Acid", Lipids, 1986, vol. 21, No. 7, pp. 430-431.

Sei-ichi Ueno et al., "On the Ocurence of New Highly Unsaturated Fatty Acids, $C_{26}H_{42}O_2$, In Tunny Oil", Bulletin of the Chemical Society of Japan, 1936, vol. 11, Issue 7, pp. 437-442.

Sei-ichi Ueno et al., "On the Oil of Hokke (Pleurogrammus Monopterygius, Pallas), With Special Reference to the Occurrence of New Highly Unsaturated $C_{28}$-Fatty Acids", Bulletin of the Chemical Society of Japan, 1936, vol. 11, Issue 10, pp. 643-649.

Yoshiyuki Toyama et al., "The Highly Unsaturated Acids in Sardine Oil X. The Separation of Highly Unsaturated C22-Acids", Bulletin of the Chemical Society of Japan, 1935, vol. 10, Issue 10, pp. 433-440.

Yoshiyuki Toyama et al., "The Highly Unsaturated Acids in Sardine Oil X. The Separation of Highly Unsaturated $C_{24}$-Acids", Bulletin of the Chemical Society of Japan, 1935, vol. 10, Issue 11, pp. 543-547.

Harald Breivik, "Long-Chain Omega-3 Specialty Oils", The Oily Press, 2007, Ch. 5, pp. 111-140.

Peter D. Nichols et al., "Occurrence of High Levels of Tetracosahexaenoic Acid in the Jellyfish *Aurelia* sp.", Lipids, 2003, vol. 38, No. 11, pp. 1207-1210.

Soonkap Halm et al., "Unusual Pattern of Fatty Acid Biosynthesis Evidence for C-19 Desaturase Activity in Freshwater Sponges", The Journal of Biological Chemistry, 1989, vol. 264, No. 35, Issue of Dec. 15, pp. 21043-21046.

Ghulam M. Maharvi et al., "Chemical synthesis of deuterium-labeled and unlabeled very long chain polyunsaturated fatty acids", Tetrahedron Lett., 2010, vol. 51, No. 49, pp. 6426-6428.

Adrianus J de Koning, "Properties of South African fish oils: A review", International Journal of Food Properties, 1999, vol. 2, No. 3, pp. 205-216.

* cited by examiner

VERY LONG CHAIN POLYUNSATURATED FATTY ACIDS FROM NATURAL OILS

FIELD OF THE INVENTION

In one aspect, the present invention is directed to a method of producing a composition comprising a high concentration of very long chain polyunsaturated fatty acids (VLCPUFAs) from natural oils such as fish oil, squid oil, algal oil and krill oil. In other aspects this invention is directed to a composition comprising a high concentration of very long chain polyunsaturated fatty acids isolated from such natural sources; as well as to a process for isolating separate fractions of very long chain polyunsaturated fatty acids having identical chain lengths but different degrees of unsaturation from such highly concentrated compositions.

BACKGROUND OF THE INVENTION

Among the long-chain polyunsaturated fatty acids (LCPUFAs), and especially long-chain omega-3 fatty acids (LCn3), the fatty acids of chain length C20-C22 have received most interest in literature. The acronyms EPA (for eicosapentaenoic acid) and DHA (for docosahexaenoic acid) have become household names in describing valuable omega-3-acids from fish oil and other sources. Products rich in alpha-linoleic acid (ALA) from plant sources are also available in the market. In this regard, it is noted that lipids are described by the formula X:YnZ wherein X is the number of carbon atoms in their alkyl chain, and Y is the number of double bonds in such chain; and where "nZ" is the number of carbon atoms from the methyl end group to the first double bond. In nature the double bonds are all in the cis-form. In polyunsaturated fatty acids each double bond is separated from the next by one methylene ($-CH_2$) group. Using this nomenclature, EPA is 20:5n3; DHA is 22:6n3 and ALA is C18:3n3. Further, as is employed herein, the term very long chain polyunsaturated fatty acids (or VLCPUFAs) is intended to mean polyunsaturated fatty acids (or PUFAs) having a chain length of more than 22 carbon atoms; the term very long chain monounsaturated fatty acids (or VLCMUFAs) is intended to mean monounsaturated fatty acids (or MUFAs) having a chain length of more than 22 carbon atoms; while the term VLCn3 is intended to refer to polyunsaturated omega-3 fatty acids having a chain length of more than 22 carbon atoms, it being understood that VLCn3 represents a sub-group of VLCPUFA.

In order to produce marine omega-3-concentrates rich in EPA and DHA, conventional industrial processes are designed to concentrate the C20-C22 fraction, by removing both short-chain fatty acids as well as larger molecules than the C22 fatty acids. Examples of such processes are molecular/short path distillation, urea fractionation, extraction and chromatographic procedures, all of which can be utilized to concentrate the C20-22 fraction of marine fatty acids and similar materials derived from other sources. A review of these procedures is provided in Breivik H (2007) Concentrates. In: Breivik H (ed) Long-Chain Omega-3 Specialty Oils. The Oily Press, PJ Barnes & Associates, Bridgwater, UK, pp 111-140.

Omega-3-acids are very liable to oxidation. In order to comply with pharmacopoeia and voluntary standards imposing upper limits for oligomeric/polymeric oxidation products, it is common to remove components with chain length above that of DHA, for example by distillation, extraction and similar procedures. Further, such higher molecular weight components of marine oils are typically associated with undesirable unsaponifiable constituents of such oil including cholesterol as well as with organic pollutants such as brominated diphenyl ethers.

However, biologically active PUFAS, including omega-3 acids are not limited to the C22 chain length of DHA. According to Poulos (Poulos A (1995) *Very long chain fatty acids in higher animals—a review*, Lipids 30:1-14) it is likely that VLCPUFA are normal components of most animal cells, but sensitive analytical procedures may be required to detect them in some tissues. Somewhat similarly, Poulos et al (*The occurrence of polyenoic fatty acids with greater than* 22 *carbon atoms in mammalian spermatozoa*, Biochem J. (1986) 240; 891-895) discloses that VLCPUFAs are found in a variety of mammalian spermatozoa (including human); while Rotstein et al (*Synthesis of very long chain* (*up to* 36 *carbon*) *tetra, penta and hexaenoic fatty acids in retina*, Biochem J. (1988) 249, 191-200) discloses the isolation of certain VLCPUFAs from bovine retina.

According to the American Oil Chemist's' Society's Lipid Library VLCPUFA of both the omega-3 and omega-6 families occur in the retina, brain and sperm (http://lipidlibrary.aocs.org/Lipids/fa_poly/index.htm). As recently as Nov. 20, 2014 the American Oil Chemist's' Society's Lipid Library was up-dated with a review on the metabolism of VLCPUFAs in mammals. (http://aocs.files.cmsplus.com/AnnualMeeting/images/lipidimporthtml/lipidlibrary/Lipids/fa_poly/index.htm). This review gives information that VLCPUFAs are isolated within the mammalian body to retinal tissue, testes, brain, and spermatozoa. Further, this review provides very useful information on valuable physiological roles of VLCPUFAs, including their importance for optimal functioning of the eyes and cerebral tissues as well as for male fertility. On the other hand, the review states that, unlike LCPUFAs, VLCPUFAs cannot be obtained from dietary sources, and thus must be synthesised in situ from shorter chain fatty acid precursors.

As a consequence of this belief, much work has focused upon the production of VLCPUFAs using recombinant techniques. For example, Anderson et al (US 2009/0203787A1, US 2012/0071558A1 and US 2014/0100280A1) disclose a recombinant process for producing C28-C38 VLCPUFAs using the ELOVL4 gene. Pertinently, Anderson et al indicate (in paragraph 13 of US 2009/0203787A1) that such recombinant processes are necessary as VLCPUFAs are only naturally found in extremely small quantities in a few organs or certain animal species, stating that "In order to obtain even minute μg quantities of these VLC-PUFAs, they must be extracted from natural sources such as bovine retinas. As a result, research into C28-C38 VLC-PUFAs has been limited, and means for commercial production thereof have been non-existent."

Consequently, it is completely unexpected that certain of these VLCPUFAs could be extracted from marine oils in commercially useful amounts; including from compositions which have in the past been considered a waste product of EPA/DHA composition production processes.

SUMMARY OF THE INVENTION

In one aspect, the present invention is directed to a method for obtaining an enriched composition of very long chain polyunsaturated fatty acids from a natural oil composition comprising the steps of:

A) Hydrolyzing an oil composition derived from natural sources and comprising very long chain polyunsaturated fatty acids with a base in the presence of an organic solvent selected from the group consisting of $C_1$-$C_5$ alcohols and ketones of the formula $R^1(C=O)R^2$ wherein $R^1$ and $R^2$ are each independently $C_1$-$C_5$ alkyl, and water to form a composition comprising free fatty acid salts of very long chain polyunsaturated fatty acids;

B) Reacting the composition comprising free fatty acid salts of very long chain polyunsaturated fatty acids formed in step A) with an acid to form a composition comprising very long chain polyunsaturated free fatty acids; and C) Concentrating the very long chain polyunsaturated fatty acids present in the composition comprising very long chain polyunsaturated free fatty acids to produce an enriched composition comprising at least 5% by weight of very long chain polyunsaturated fatty acids.

In another aspect, the present invention is directed to a method for obtaining an enriched composition of very long chain polyunsaturated fatty acids from a natural oil composition comprising the steps of:

a) Hydrolyzing an oil composition derived from natural sources and comprising very long chain polyunsaturated fatty acids with a base in the presence of an organic solvent selected from the group consisting of $C_1$-$C_5$ alcohols and ketones of the formula $R^1(C=O)R^2$ wherein $R^1$ and $R^2$ are each independently $C_1$-$C_5$ alkyl, and water to form a composition comprising free fatty acid salts of very long chain polyunsaturated fatty acids;

b) Subjecting such composition to conditions such that (i) a precipitate and (ii) a filtrate comprising free fatty acid salts of very long chain polyunsaturated fatty acids, are formed;

c) Removing the precipitate to obtain a filtrate comprising free fatty acid salts of very long chain polyunsaturated fatty acids;

d) Reacting the filtrate comprising free fatty acid salts of very long chain polyunsaturated fatty acids with an acid to form a composition comprising very long chain polyunsaturated free fatty acids; and e) Concentrating the very long chain polyunsaturated fatty acids present in the composition comprising very long chain polyunsaturated free fatty acids to produce an enriched composition comprising at least 5% by weight of very long chain polyunsaturated fatty acids.

In a further aspect, the present invention is directed to a process for isolating separate fractions of very long chain polyunsaturated fatty acids having identical chain lengths but different degrees of unsaturation employing urea fractionation.

In another aspect, the present invention is directed to an enriched composition comprising at least 5% by weight of very long chain polyunsaturated fatty acids derived from fish oil, squid oil, krill oil or algal oil.

In yet another aspect, this invention is directed to a nutraceutical or pharmaceutical composition comprising (a) at least 5% by weight of very long chain polyunsaturated fatty acid; and (b) at least 5% by weight of one or more $C_{20}$-$C_{22}$ polyunsaturated fatty acids.

DETAILED DESCRIPTION OF THE INVENTION

In one aspect, the present invention is directed to a method for obtaining an enriched composition of very long chain polyunsaturated fatty acids from a natural oil composition comprising the steps of:

A) Hydrolyzing an oil composition derived from natural sources and comprising very long chain polyunsaturated fatty acids with a base in the presence of an organic solvent selected from the group consisting of $C_1$-$C_5$ alcohols and ketones of the formula $R^1(C=O)R^2$ wherein $R^1$ and $R^2$ are each independently $C_1$-$C_5$ alkyl, and water to form a composition comprising free fatty acid salts of very long chain polyunsaturated fatty acids;

B) Reacting the composition comprising free fatty acid salts of very long chain polyunsaturated fatty acids formed in step A) with an acid to form a composition comprising very long chain polyunsaturated free fatty acids; and C) Concentrating the very long chain polyunsaturated fatty acids present in the composition comprising very long chain polyunsaturated free fatty acids to produce an enriched composition comprising at least 5% by weight of very long chain polyunsaturated fatty acids.

Typically, the composition comprising free fatty acid salts of very long chain polyunsaturated fatty acids produced in step A) is subjected to conditions such that a precipitate if formed; and such precipitate is removed, thereby forming a filtrate, prior to step B). Accordingly, in such aspect, the present invention is directed to a method for obtaining an enriched composition of very long chain polyunsaturated fatty acids from a natural oil composition comprising the steps of:

a) Hydrolyzing an oil composition derived from natural sources and comprising very long chain polyunsaturated fatty acids with a base in the presence of an organic solvent selected from the group consisting of $C_1$-$C_5$ alcohols and ketones of the formula $R^1(C=O)R^2$ wherein $R^1$ and $R^2$ are each independently $C_1$-$C_5$ alkyl, and water to form a composition comprising free fatty acid salts of very long chain polyunsaturated fatty acids;

b) Subjecting such composition to conditions such that (i) a precipitate and (ii) a filtrate comprising free fatty acid salts of very long chain polyunsaturated fatty acids are formed;

c) Removing the precipitate to obtain a filtrate comprising free fatty acid salts of very long chain polyunsaturated fatty acids;

d) Reacting the filtrate comprising free fatty acid salts of very long chain polyunsaturated fatty acids with an acid to form a composition comprising very long chain polyunsaturated free fatty acids; and e) Concentrating the very long chain polyunsaturated fatty acids present in the composition comprising very long chain polyunsaturated free fatty acids to produce an enriched composition comprising at least 5% by weight of very long chain polyunsaturated fatty acids.

Preliminarily, it is noted that step A) of the three step process (i.e., that process which does not require the formation and removal of a precipitate prior to acidification in step B)) is equivalent to step a); step B) is equivalent to step d); and step C) is equivalent to step e). Accordingly, in the description below, the description of step a) is equally applicable to step A); the description of step d) is equally applicable to step B); and the description of step e) is equally applicable to step C, respectively.

The oil composition comprising very long chain polyunsaturated fatty acids which is hydrolyzed in step a) (or Step A)) may be derived from any natural source containing very long chain polyunsaturated fatty acids, including but not limited to fish, crustaceans such as krill, algae, plankton, and higher plants. Without limiting the choice of raw materials, such starting material is typically obtained by transesterification oil obtained from fish of families such as Engraulidae, Carangidae, Clupeidae, Osmeridae, Salmonidae and Scombridae or from animals of the class Cephalopoda and subsequent physico-chemical purification processes. Specific fish species from which such oil may be derived include herring, capelin, anchovy, mackerel, blue whiting, sand eel, squid, cod viscera and pollock viscera.

In certain embodiments, the starting oil composition has a reduced amount of fatty acids having a chain length of $C_{18}$ or less ("shorter chain fatty acids"), many of which are saturated fatty acids, due to such starting oil composition having been subjected to a prior concentration step (such as short path distillation or extraction) to remove such shorter chain fatty acids from such composition. As most of the saturated fatty acids of marine oil typically have relatively short chain lengths (in herring oil mostly $C_{14}$ and $C_{16}$) such a procedure will also significantly reduce the content of saturated fatty acids in the starting material.

One preferred starting material is the residue from the second step of a traditional two-step short path/molecular distillation procedure for the manufacture of omega-3-concentrates. At present this residue represents a low value by-product from traditional processing. Thus, omega-3 acid concentrates with about a 60% by weight omega-3 concentration are typically manufactured by a two-step short path distillation of ethylated marine oil:
1. In the first step the content of ethyl esters of fatty acids with chain length up to C18 is reduced.
2. In the second step the residue from the first step is passed through a distillation unit in order to isolate a distillate rich in omega-3 acids, particularly EPA and DHA. In the case of an ethyl ester concentrate this distillate may be the final product. If the final product is to be marketed as a triglyceride product, a further transesterification step with glycerol is required.

The residue from such second distillation or subsequent distillations contains a high amount of partial glycerides and is enriched in cholesterol. The commercial value of such residue is today very low. However, such residue will contain most of the VLCPUFAs of the original oil, in addition to high concentrations of DHA and EPA. Surprisingly, by treating such residue according to the present invention, a free fatty acid product can be obtained that includes not only the VLCPUFAs, but is also rich in DHA and/or EPA and/or other $C_{18}$-$C_{22}$ omega-3 acids, notably DPA (22:5n3).

In other embodiments, the starting oil composition will not have had shorter chain fatty acids removed prior to hydrolysis in step a) (or Step A)). In such embodiments, shorter chain fatty acids are typically removed subsequent to the hydrolysis of the starting oil composition in step a) (or step A)) employing processes such as distillation, extraction, enzymatic fractionation procedures and/or chromatography which are known to those of skill in the art. Such removal may occur from the composition comprising free fatty acid salts of very long chain polyunsaturated fatty acids or the composition comprising free fatty acids of very long chain polyunsaturated fatty acids.

In step a) (or step A)) of the process of this invention, the oil composition is hydrolyzed by reaction with a base in the presence of an organic solvent selected from the group consisting of $C_1$-$C_5$ alcohols and ketones of the formula $R^1(C=O)R^2$ wherein $R^1$ and $R^2$ are each independently $C_1$-$C_5$ alkyl, and water to form a composition comprising free fatty acid salts of $C_{24}$-$C_{28}$ very long chain polyunsaturated fatty acids.

The organic solvent employed is selected from the group consisting of $C_1$-$C_5$ alcohols and ketones of the formula $R^1(C=O)R^2$ wherein $R^1$ and $R^2$ are each independently $C_1$-$C_5$ alkyl. Such solvent is generally added in an amount of between 0.5 and 8 liters, preferably between 1 and 4 liters, per kilogram of oil composition. The amount of water present will depend upon the particular reactants selected and can be readily optimized by one of ordinary skill in the art.

Typically, the base employed comprises potassium hydroxide, although other bases such as sodium hydroxide, lithium hydroxide, potassium carbonate, sodium carbonate, lithium carbonate, potassium bicarbonate, sodium bicarbonate and lithium bicarbonate may also be employed. Such base(s) is added in an amount sufficient to obtain a complete hydrolysis of the oil. A benefit of using potassium hydroxide is that it can readily be dissolved both in ambient ethanol and water, adding flexibility in order to obtain the desired water content of the solvent without unnecessarily increasing the total solvent volume.

In certain embodiments, the base(s) employed comprises a lithium salt such as lithium carbonate, lithium bicarbonate or lithium hydroxide. The lithium salt may be employed as a hydrate, for example lithium hydroxide monohydrate. Such lithium salt(s) are typically employed in the form of an aqueous solution, although such salt may be added as a solid in the event that such salt is soluble in the particular organic solvent employed. Thus, for example, lithium hydroxide may be employed as a solid when ethanol is used as the organic solvent. In such embodiments, the oil composition, lithium salt and organic solvent are blended until lithium salts of saturated and monounsaturated fatty acids present in the oil composition are formed. Such blending may range from several minutes or less to several hours or more, depending upon factors such as: the volume and concentration of the components, the particular components selected, the extent of agitation employed, the temperature selected, and the like. Typically, the components are mixed at a temperature of between about 15° C. and 80° C. for a period of between a few minutes up to 24 hours.

In optional step b), the composition comprising free fatty acid salts of very long chain polyunsaturated fatty acids formed in step a) is then subjected to conditions such a precipitate is formed. Typically, this involves cooling (or letting such composition cool) to a temperature of ambient or less than ambient, such as 10° C. of less and even to about 0° C. or less. An alternative procedure in order to remove the monounsaturated fatty acids and other undesired components would also be to remove the precipitate that is formed at a relative high temperature, for example at 10-30° C., and then to reduce the volume of the reaction mixture in one or more steps by suitable evaporative processes before removal of one or several further fractions of precipitate. Once the precipitate has formed, the precipitate is removed in step c) to obtain a filtrate comprising free fatty acid salts of very long chain polyunsaturated fatty acids. If desired, in the event that a lithium salt and a suitable starting material containing very long chain monounsaturated fatty acids (VLCMUFAs) are employed in step a), such VLCMUFAs can be recovered for commercial use from the precipitate.

Optionally, either (i) the composition comprising free fatty acid salts of very long chain polyunsaturated fatty acids produced in step a) or (ii) the filtrate comprising free fatty acid salts of very long chain polyunsaturated fatty acids produced in step c) may be treated with a lipophilic solvent to reduce the amount of unsaponifiable material present. Due to their lipophilic character, materials such as cholesterol as well as the pollutants like DDT, PCB, dioxins and PBDE are typically associated with such unsaponifiable material. Lipophilic solvents which are typically employed include ethyl acetate, hexane and carbon dioxide. The lipophilic solvent could also include esters of fatty acids, for example fatty acids ethyl esters or fatty acid triglycerides.

This latter group of solvent could include fatty acid ethyl ester (fractions) from fish oil and other edible oils as well as fish oil or edible oil triglycerides (for example, soybean oil).

In step d) of the process of this invention, the flitrate comprising free fatty acid salts of very long chain polyunsaturated fatty acids is reacted with an acid to form a composition comprising very long chain polyunsaturated free fatty acids. (In step B, the composition comprising free fatty acid salts of very long chain polyunsaturated fatty acids formed in step A) is reacted with an acid.) Acids which are typically employed include citric acid, hydrochloric acid, sulfuric acid and the like.

The free VLCPUFAs formed in step d) (or step B)) are then concentrated to form enriched compositions of very long chain polyunsaturated fatty acids. Such concentration may be accomplished employing processes such as distillation, extraction, enzymatic processing, chromatography and/or other fractionation methods known to one of skill in the art. Employing such technologies, compositions containing 5%, 10%, 15%, 20%, 30% or more VLCPUFA by weight can be obtained.

In another aspect, the present invention is directed to a method of separating VLCPUFAs having different degrees of unsaturation by employing urea fractionation. In this regard, it is well known in the art that urea fractionation represents a valuable tool for commercial manufacture of concentrates of C20-C22 omega-3 fatty acids, like EPA and DHA. Specifically, urea fractionation is typically employed to remove saturated and lesser unsaturated fatty acids from such PUFAs, resulting in an increased concentration of such PUFAs. Surprisingly, it has been found that urea fractionation is ineffective to similarly increase the total concentration of VLCPUFAs. In addition to the removal of high molecular weight components by distillation, this may be one reason why significant concentrations of VLCPUFAs are not observed in commercial omega-3 concentrates.

It has been unexpectedly found, however, that urea fractionation may be effectively employed to achieve isolated fractions of fatty acids within each group of VLCPUFAs with identical chain length. Thus, by using urea as a fractionation tool, the relative content of the most unsaturated VLCPUFAs within each chain length may be increased in the non-urea complexing fraction, while the relative content of the less unsaturated VLCPUFAs at the same time may be increased in the urea complexing fraction of the fatty acids. Thus, for example, the fatty acids with the lowest number of double bonds can be step-wise isolated from a mixture comprising C28:4n3, C28:5n3, C28:6n3, C28:7n3 and C28:8n3 VLCPUFAs as urea adducts (UA), while the fatty acids with the highest degree of unsaturation, especially C28:8n3, remain in the non-urea adduct (NUA) fraction to a large extent. Employing such techniques, compositions comprising at least 5% by weight; at least 8% by weight or at least 10% by weight of C28:7 and/or C28:8 very long chain polyunsaturated fatty acids can be produced. At the same time fractions enriched in C28:4n3, C28:5n3 and/or C28:6n3 may also be produced. Similarly, compositions comprising fractions enriched in C24:5n3 and/or C24:6n3 may also be produced.

Such urea fractionation is conducted under conditions typically employed for the relevant starting material, which conditions are well known or can be readily determined by one of skill in the art. In this regard, the use of urea fractionation is disclosed in EP 255,824 B1 and in Breivik H (2007) Concentrates; in Breivik H (ed) Long-Chain Omega-3 Specialty Oils. The Oily Press, PJ Barnes & Associates, Bridgwater, UK, pp 111-140, the disclosures of which are hereby incorporated by reference. Urea is typically added in amounts (ranging from 0.3 to 5 parts by weight per part of weight of oil) under reaction conditions (for example at temperature between ambient and 80° C.) for periods of time typically employed in the concentrate of commercial concentrated PUFA compositions.

In another aspect, this invention is directed to enriched composition comprising at least 5% by weight of very long chain polyunsaturated fatty acids derived from fish oil, squid oil, krill oil or algal oil. Typically, such compositions may comprise more than 10%, more than 20%, more than 30%, more than 40%, more than 50%, more than 60%, or more than 70% by weight of very long chain polyunsaturated fatty acids. Such compositions may be in the form of free fatty acids, or by employing processes well known to one of ordinary skill in the art may comprise very long chain polyunsaturated fatty acids in the form of ethyl esters and/or triglycerides.

In yet another aspect, this invention is directed to a nutraceutical or pharmaceutical composition comprising (a) at least 5% by weight of very long chain polyunsaturated fatty acid; and (b) at least 5% by weight of one or more $C_{20}$-$C_{22}$ polyunsaturated fatty acids. In certain embodiments, such composition may comprise at least 10%, at least 15%, or at least 20% or more by weight of very long chain polyunsaturated fatty acid. In certain embodiments, such compositions of this invention comprise at least 25%, at least 30%; at least 40%, at least 50%, at least 60%, or at least 70% by weight of $C_{20}$-$C_{22}$ long chain polyunsaturated fatty acids. Further, in other embodiments, the compositions of this invention comprise at least 5%, at least 8%; or at least 10% by weight of DPA (22:5n3). Such nutraceutical or pharmaceutical compositions may be in the form of free fatty acids, or by employing processes well known to one of ordinary skill in the art, may comprise very long chain polyunsaturated fatty acids and/or $C_{20}$-$C_{22}$ long chain polyunsaturated fatty acids in the form of ethyl esters and/or triglycerides.

It is to be understood that each component, compound, substituent, or parameter disclosed herein is to be interpreted as being disclosed for use alone or in combination with one or more of each and every other component, compound, substituent, or parameter disclosed herein.

It is also to be understood that each amount/value or range of amounts/values for each component, compound, substituent, or parameter disclosed herein is to be interpreted as also being disclosed in combination with each amount/value or range of amounts/values disclosed for any other component(s), compounds(s), substituent(s), or parameter(s) disclosed herein and that any combination of amounts/values or ranges of amounts/values for two or more component(s), compounds(s), substituent(s), or parameters disclosed herein are thus also disclosed in combination with each other for the purposes of this description.

It is further understood that each lower limit of each range disclosed herein is to be interpreted as disclosed in combination with each upper limit of each range disclosed herein for the same component, compounds, substituent, or parameter. Thus, a disclosure of two ranges is to be interpreted as a disclosure of four ranges derived by combining each lower limit of each range with each upper limit of each range. A disclosure of three ranges is to be interpreted as a disclosure of nine ranges derived by combining each lower limit of each range with each upper limit of each range, etc. Furthermore, specific amounts/values of a component, compound, substituent, or parameter disclosed in the description or an example is to be interpreted as a disclosure of either a lower or an upper limit of a range and thus can be combined with any other lower or upper limit of a range or specific amount/value for the same component, compound, substituent, or parameter disclosed elsewhere in the application to form a range for that component, compound, substituent, or parameter.

EXAMPLES

The following Examples are provided to illustrate the invention in accordance with the principles of this invention, but are not to be construed as limiting the invention in any way except as indicated in the appended claims. In such Examples, all percentages are by weight unless specified otherwise; for example, in the Tables fatty acid content is analyzed as GC area %. Further, fatty acid analysis was only completed for fatty acids having a length of C30 or less.

Example 1

Herring oil was reacted to form ethyl esters. The ethyl esters were passed once through a short path distillation apparatus in order to reduce the content of shorter chain fatty acid ethyl esters. A residue of 19% was collected and utilized as starting material for the next fractionation step.

40 grams of this residue were dissolved in 40 ml 96% ethanol and reacted with 24 ml 5N KOH and 48 ml 5N LiOH. The reaction mixture was kept at 40° C. overnight, and then cooled in an ice bath for 4 hours. After removal of precipitated lithium salts by filtration, the filtrate was acidified with aqueous citric acid and 5.54 g free fatty acids were isolated (14% yield).

GC chromatography showed two peaks eluting well after DHA, and in concentrations of 6.0 and 1.6 area %. Based on GC/MS-analysis these two peaks were identified as C24:5n3 and C24:6n3 respectively. By running the GC/MS-chromatogram for a longer time than for conventional analyses of omega-3 acids further peaks were observed.

Example 2

The content of the ethyl esters of short chain fatty acids of the ethylated herring oil described in column 2 of Table 1 was reduced by a two-step distillation procedure, using short path distillation (VTA, model VK83-6-SKR-G with degasser). The first distillation took place at temperature of 113° C., a flow of 7.4 kg/h and a vacuum of 0.01 mbar. This procedure gave a distillate of 30.1% and a residue of 69.9%. The residue from this distillation was passed once more through the distillation still, using the same flow and vacuum, but this time at a temperature of 152° C. A distillate of 70.5% and a residue of 29.5% was obtained. The composition of ethyl esters of this second distillation residue is given in column 3 of Table 1 below.

Two portions of 1.00 kg of the second distillation residue were each hydrolyzed in a mixture of 1000 ml 96% ethanol, 400 ml aqueous 5N potassium hydroxide and 1400 ml aqueous 5 N lithium hydroxide. After a reaction time of 4 hours at 40° C. the resulting reaction mixtures were stored in an ice bath until the next morning. After removal of the precipitates by filtration, the filtrates were acidified with 4N hydrochloric acid to separate out free fatty acids, and a total of 363.2 g product (36.3%) was isolated. The fatty acid composition of this filtrate is set forth in column 4 of Table 1.

This product was distilled using a short path distillation still (Leybold KDL 4) at a temperature of 145° C. a flow of 4.1 ml/min and a pressure of $10^{-3}$-$10^{-4}$ mbar (for practical reasons two distillations were performed, each under identical conditions). This gave a combined distillate of 65% and a residue of 35%. The residue from this distillation was passed once more through the same distillation still, using the same vacuum, but this time at a temperature of 133° C. and a flow of about 3.5 ml. This final distillation gave a distillate of 55% and a residue of 45%. The composition of ethyl esters of this second distillation distillate and residue is given in column 5 of Table 1.

TABLE 1

VLC PUFA from herring oil.

|  | 2 | 3 | 4 | 5 Results from short path distillation A first residue from 145° C. (35%) was redistilled at 133° C. | |
| --- | --- | --- | --- | --- | --- |
| Column 1 Fatty acid | Ethylated herring oil | Second Distillation Residue | PUFA concentrate (free fatty acids) after Li fractionation | Distillate 55% | Residue 45% |
| C14:0 | 7.4 | 0.3 | 0.3 | 0.0 | 0.0 |
| C16:0 | 12.5 | 0.8 | 0.3 | 0.0 | 0.0 |
| C16:1n7 | 5.0 | 0.3 | 0.9 | 0.1 | 0.0 |
| C16:4n1 | 0.4 | 0.0 | 0.0 | 0.0 | 0.0 |
| C18:0 | 1.0 | 0.2 | 0.0 | 0.0 | 0.0 |
| C18:1n9 | 10.9 | 1.4 | 4.0 | 0.7 | 0.1 |
| C18:1n7 | 1.5 | 0.2 | 0.2 | 0.0 | 0.0 |
| C18:2n6 | 1.4 | 0.2 | 0.6 | 0.0 | 0.0 |
| C18:3n3 | 0.9 | 0.1 | 0.4 | 0.0 | 0.0 |
| C18:4n3 | 2.6 | 0.3 | 1.0 | 0.2 | 0.0 |
| C20:1n11 |  |  | 2.7 | 2.0 | 0.5 |
| C20:1n9 | 13.9[1] | 11.7[1] | 2.7 | 2.1 | 0.6 |
| C20:1n7 | — | 0.3 | 0.3 | 0.0 | 0.0 |
| C20:4n6 | — | 0.0 | 0.3 | 0.1 | 0.0 |
| C20:4n3 | 0.5 | 0.3 | 1.2 | 0.2 | 0.2 |
| C20:5n3 | 6.9 | 3.9 | 14.0 | 8.9 | 2.0 |
| C21:5n3 | 0.3 | 0.4 | 1.4 | 1.4 | 0.5 |
| C22:1(n13 + n11) | 22.9[2] | 56.3[2] | 3.8 | 4.8 | 4.5 |
| C22:1n9 | — | — | 1.0 | 1.2 | 1.2 |
| C22:5n6 | — | 0.2 | 0.5 | 0.9 | 0.6 |

TABLE 1-continued

VLC PUFA from herring oil.

| Column 1 Fatty acid | 2 Ethylated herring oil | 3 Second Distillation Residue | 4 PUFA concentrate (free fatty acids) after Li fractionation | 5 Results from short path distillation A first residue from 145° C. (35%) was redistilled at 133° C. Distillate 55% | Residue 45% |
|---|---|---|---|---|---|
| C22:5n3 | 0.6 | 1.3 | 4.7 | 5.9 | 4.2 |
| C22:6n3 | 7.0 | 13.8 | 47.8 | 58.8 | 40.7 |
| C24:1 | 0.8 | 3.4 | 0.7 | 0.8 | 3.4 |
| C24:4n3[3] | | | | | 0.63[3] |
| C24:5 n3 | 0.35 | 1.21 | 3.86 | 4.62 | 10.71 |
| C24:6n3 | 0.13 | 0.47 | 1.31 | 1.60 | 3.71 |
| C26:4n3 | 0.06 | 0.26 | 0.33 | 0.23 | 1.64 |
| C26:5n3 | | 0.06 | 0.10 | 0.08 | 0.50 |
| C26:6n3 | | 0.27 | 0.27 | 0.23 | 1.23 |
| C26:7n3 | | 0.07 | 0.11 | 0.10 | 0.45 |
| C28:4n3 | | | | | 0.30 |
| C28:5n3 | | | | 0.02 | 0.65 |
| C28:6n3 | | 0.11 | 0.37 | 0.16 | 2.16 |
| C28:8n3 | 0.13 | 0.54 | 1.92 | 0.98 | 11.17 |
| C30:5n3 | | | | | 0.15 |
| C30:6n3 | | | | | 0.81 |
| Sum VLCn3 | 0.67 | 2.99 | 8.27 | 8.02 | 34.01 |
| Sum n3 | 19.5 | 23.1 | 78.8 | 83.4 | 83.6 |

[1]Including C20:1n11
[2]Including C22:1n9
[3]Only analyzed in final product
Results in GC area %. It is noted that for the starting and intermediate oils several of the VLCPUFAS were present below the quantification limits The lithium fractionated product in column 3 of Table 1 contained about 8.3% of quantified VLCn3s, and a total of 78.8% omega-3 acids (all analyzed as GC area %). The residue after the second distillation of this product contained 34% identified C24-C30 VLCn3s and a total of 83.6% omega-3 acids. Also the distillate contained above 83% omega-3 acids, of which were 8% identified VLCn3s.

The skilled person will realize that all the above products may be further purified before use, for example by adsorption, extraction, distillation or chromatographic procedures.

Example 3

The same herring oil starting material employed in Example 2 was subjected to the two-step initial distillation process described in such Example to obtain a second distillation residue (the analysis of the starting herring oil and of the second distillate are presented in columns 2 and 3 of Table 2, respectively).

300 g of the second distillation residue was hydrolyzed in a mixture of 1000 ml 96% ethanol containing 40 g sodium hydroxide. After a reaction time of 1 hour at 80° C. the resulting reaction mixtures was cooled to 20° C. After removal of the precipitates by filtration, the filtrates were acidified with an excess of citric acid in water to separate out free fatty acids, and a total of 47.2 g product was isolated. This procedure was repeated to obtain more material for distillation. The composition of this filtrate is set forth in column 4 of Table 2.

This product (90 g) was distilled using a short path distillation still (VTA, model VKL-70-4-SKR-T) at a temperature of 110° C. a flow of 5.5 ml/min and a pressure of $10^{-3}$ mbar. The residue from this distillation was passed twice through the same distillation still, at 125° C. at a flow of 5.5 ml/min and a pressure of $10^{-3}$ mbar. The distillation gave a final residue of 29 g. The composition of ethyl esters of this final distillation residue is given in column 5 of Table 2.

TABLE 2

VLC PUFA from herring oil.

| Column 1 Fatty acid | 2 Ethylated herring oil | 3 Second Distillation Residue | 4 PUFA concentrate (free fatty acids) after Na fractionation | 5 Results from short path distillation Residue |
|---|---|---|---|---|
| C14:0 | 7.4 | 0.3 | 2.23 | 0.03 |
| C16:0 | 12.5 | 0.8 | 2.49 | 0.06 |
| C16:1n7 | 5.0 | 0.3 | 0.08 | |
| C16:4n1 | 0.4 | 0.0 | 0.21 | 0.09 |
| C18:0 | 1.0 | 0.2 | 3.76 | 0.33 |
| C18:1n9 | 10.9 | 1.4 | 0.43 | 0.1 |
| C18:1n7 | 1.5 | 0.2 | 0.09 | |
| C18:2n6 | 1.4 | 0.2 | 0.67 | |
| C18:3n3 | 0.9 | 0.1 | 00.1 | 0.32 |

TABLE 2-continued

VLC PUFA from herring oil.

| Column 1 Fatty acid | 2 Ethylated herring oil | 3 Second Distillation Residue | 4 PUFA concentrate (free fatty acids) after Na fractionation | 5 Results from short path distillation Residue |
|---|---|---|---|---|
| C18:4n3 | 2.6 | 0.3 | 2.13 | 0.91 |
| C20:1n11 | | | | |
| C20:1n9 | 13.9[1] | 11.7[1] | 4.29 | 3.73 |
| C20:1n7 | — | 0.3 | 0.13 | 0.12 |
| C20:4n6 | — | 0.0 | 0.6 | 0.28 |
| C20:4n3 | 0.5 | 0.3 | 1.09 | 0.77 |
| C20:5n3 | 6.9 | 3.9 | 18.54 | 10.86 |
| C21:5n3 | 0.3 | 0.4 | 1.35 | 1.38 |
| C22:1(n13 + n11) | 22.9[2] | 56.3[2] | 0.52 | 1.19 |
| C22:1n9 | — | — | | |
| C22:5n6 | — | 0.2 | 0.68 | 0.36 |
| C22:5n3 | 0.6 | 1.3 | 3.1 | 4.24 |
| C22:6n3 | 7.0 | 13.8 | 37.92 | 52.74 |
| C24:1 | 0.8 | 3.4 | 0.35 | 0.95 |
| C24:4n3[3] | | | | |
| C24:5 n3 | 0.35 | 1.21 | 1.25 | 2.52 |
| C24:6n3 | 0.13 | 0.47 | 0.69 | 1.38 |
| C26:4n3 | 0.06 | 0.26 | 0.11 | 0.25 |
| C26:5n3 | | 0.06 | 0.03 | 0.07 |
| C26:6n3 | | 0.27 | 0.1 | 0.23 |
| C26:7n3 | | 0.07 | 0.06 | 0.11 |
| C28:4n3 | | | 0.11 | 0.24 |
| C28:5n3 | | | | |
| C28:6n3 | | 0.11 | | |
| C28:8n3 | 0.13 | 0.54 | 1.07 | 2.26 |
| C30:5n3 | | | | |
| C30:6n3 | | | | |
| Sum VLCn3 | 0.67 | 2.99 | 3.42 | 7.06 |
| Sum n3 | 19.5 | 23.1 | 67.55 | 78.28 |

[1]Including C20:1n11
[2]Including C22:1n9
[3]Only analyzed in final product
Results in GC area %. It is noted that for the starting and intermediate oils several of the VLCPUFAS were present below the quantification limits.

The sodium fractionated product in column 4 of Table 2 contained about 3.42% of quantified VLCn3s, and a total of 67.55% omega-3 acids (all analyzed as GC area %). The final residue after distillation of this product contained 7.06% identified C24-C30 VLCn3s and a total of 78.28% omega-3 acids.

The skilled person will realize that all the above products may be further purified before use, for example by adsorption, extraction, distillation or chromatographic procedures.

Example 4

997.6 g of the residue from the final commercial scale distillation of an ethylated sardine and mackerel oil utilized to produce an omega-3-acid concentrate containing about 46% EPA and about 13% DHA (the starting material) was hydrolyzed by heating for 40° C. for 4 hours in 1.6 l 96% ethanol containing 168.6 g potassium hydroxide. After cooling in an ice bath, removal of precipitate by filtration and acidification employing an excess of hydrochloric acid, 704.4 g of an oily product was isolated. The acid value of the product was 207, showing that the product was substantially comprised of free fatty acids.

218.6 g of this product was passed through a short path distillation still (Leybold KDL 4) at 140° C. at a flow of 3.5 ml/min. The residue from this distillation, 34.9 gram (16%), had a composition as given in Table 3. The product contained 16.3% of identified VLCPUFAs, and a total of 88.3% of omega-3 acids. An important aspect of this product is that it also contains 10.4% C22:5n3 (omega-3 DPA) in addition to DHA and EPA. Omega-3 DPA (all-cis-7,10,13,16,19-docosapenatenoic acid) is an important omega-3 fatty acids, and there are very few, if any, commercially available omega-3 products that contain such high amounts of this fatty acid.

The skilled person will realize that all these products may be further purified before use, for example by adsorption, extraction, distillation or chromatographic procedures.

TABLE 3

| Fatty acid | Starting material | Residue from distillation |
|---|---|---|
| 20:4n3 | 1.33 | 0.63 |
| 20:5n3 (EPA) | 25.00 | 10.65 |
| 21:5n3 | 2.12 | 1.79 |
| 22:5n3 (n3DPA) | 7.43 | 10.40 |
| 22:6n3 (DHA) | 34.04 | 48.47 |
| 24:5n3 | 1.16 | 3.38 |
| 24:6n3 | 1.09 | 3.19 |
| 26:4n3 | 0.07 | 0.21 |
| 26:5n3 | 0.19 | 0.76 |
| 26:6n3 | 0.14 | 0.67 |
| 26:7n3 | 0.05 | 0.26 |
| 28:5n3 | 0.22 | 0.90 |
| 28:6:n3 | 0.06 | 0.35 |
| 28:7n3 | 0.08 | 0.52 |
| 28:8n3 | 0.89 | 5.79 |
| 30:5n3 | nq | 0.14 |
| 30:6n3 | nq | 0.16 |
| Sum VLCn3 | 4.00 | 16.33 |
| Sum n3 | 74.95 | 88.27 |

Results in GC area percent.
nq = not quantified

Example 5

1003 g of the same residue from the final commercial scale distillation of an ethylated sardine and mackerel oil as described in Example 4 was hydrolyzed by heating at 40° C. for 4 hours in a mixture of 1.00 l 96% ethanol, 0.400 l aqueous 5N KOH and 1.400 l aqueous 5N LiOH. After cooling overnight in an ice bath, removal of precipitate by filtration and thereafter acidification, 707.2 g of an oily product was isolated.

An important aspect of this product, that can represent the starting point for further fractionation, is that it already contains 7.4% C22:5n3 (omega-3 DPA) in addition to DHA and EPA. Omega-3 DPA (all-cis-7,10,13,16,19-docosapentaenoic acid) is an important omega-3 fatty acid, and there are very few, if any, commercially available omega-3 products that contain such high amounts of this fatty acid. In contrast to fish oil, algal oils/single cell oils often contain significant contents of another DPA acid (all-cis 4,7,10,13,16,-docosapentaenoic acid). This latter DPA acid is often confused with the beneficial omega-3 DPA, although it in reality is an omega-6 acid with very different biological effects.

This product was passed through a laboratory short path distillation still (Leybold KDL 4) at 130° C., a flow of 4.3-5.2 ml/min and a pressure of $10^{-3}$-$10^{-4}$ mbar. The distillate from this distillation, 409.8 g (42.3%) and had composition given in Table 4 (R1).

The same laboratory short path distillation apparatus, with the same pressure and column temperature, was utilized for all the subsequent distillation steps that are described below.

395.8 g of the residue from this first distillation as described above was distilled a second time, at an average flow of 5.2 ml/min. The residue from this second distillation, 117.7 g (33%) had the composition is given in Table 4 (R2).

236.7 g of the residue from the second distillation as described above was distilled a third time, at an average flow of 4.5 ml/min. The residue from this third distillation, 108.0 g (44.8%) had the composition is given in Table 4 (R3).

130.3 g of the residue from the third distillation as described above was distilled a fourth time, at an average flow of 3.4 ml/min. The residue from this fourth distillation, 36.5 g (27.9%) had the composition as given in Table 4 (R4).

The skilled person will realize that the product from hydrolysis according to the other examples herein will also be well suited for further fractionation according to the procedures as illustrated by this Example 5.

The skilled person will also realize that all the products as described in Table 4 may be further purified before use, for example by one or more adsorption, extraction, enzymatic fractionation procedures, distillation and/or chromatographic procedures.

Molecular/short path distillation represents a flexible tool for fatty acid fractionation. It will be obvious for the skilled person that by choosing different distillation designs, including different temperatures and pressures, the fatty acid fractions that were obtain could differ appreciably from those of Table 4.

TABLE 4

| Fatty Acid | Starting Material | R1 | R2 | R3 | R4 |
|---|---|---|---|---|---|
| C14:0 | 1.01 | 0 | 0 | 0.02 | 0 |
| C16:0 | 3.08 | 0.03 | 0 | 0 | 0.03 |
| C16:1 | 1.61 | 0.08 | 0 | 0.03 | 0.01 |
| C18:0 | 2.13 | 0.77 | 0.15 | 0.08 | 0 |
| C18:1n9 | 0.9 | 0.27 | 0.06 | 0 | 0 |
| C18:2n6 | 0.27 | 0.1 | 0 | 0 | 0 |
| C18:3n3 | 0.18 | 0.07 | 0 | 0 | 0 |
| C18:4n3 | 0.85 | 0.31 | 0.05 | 0 | 0 |
| C20:1n11 | 1.99 | 1.27 | 0.84 | 0.51 | 0.24 |
| C20:1n9 | 0.38 | 0.17 | 0.12 | 0.07 | |
| C20:4n6 | 1.19 | 1.02 | 0.54 | 0.29 | 0.11 |
| C20:4n3 | 1.33 | 1.28 | 0.83 | 0.5 | 0.23 |
| EPA | 25 | 22.16 | 12.3 | 7.04 | 3 |
| C22:1n11 + 13 | 3.68 | 3 | 3.77 | 4.03 | 4.28 |
| C22:1n9 | 0.66 | 0.5 | 0.65 | 0.73 | 0.77 |
| C21:5n3 | 2.12 | 2.49 | 2.21 | 1.71 | 1.26 |
| C22:5n6 | 1.05 | 1.42 | 1.55 | 1.47 | 1.38 |
| C22:5n3 | 7.43 | 10.22 | 12.51 | 12.38 | 12.18 |
| DHA | 34.04 | 46.09 | 51.52 | 50.24 | 48.78 |
| C24:1 | 2.3 | 0.32 | 0.49 | 0.81 | 1.12 |
| C24:5n3 | 1.16 | 1.79 | 2.76 | 4.24 | 5.52 |
| C24:6n3 | 1.09 | 1.68 | 2.55 | 3.86 | 5.03 |
| C26:4n3 | 0.07 | 0.06 | 0.1 | 0.19 | 0.26 |
| C26:5n3 | 0.19 | 0.23 | 0.38 | 0.73 | 1.03 |
| C26:6n3 | 0.14 | 0.25 | 0.42 | 0.77 | 1.07 |
| C26:7n3 | 0.05 | 0.1 | 0.17 | 0.31 | 0.43 |
| C28:4n3 | 0.05 | 0.17 | 0.3 | 0.66 | 0.92 |
| C28:5n3 | 0.22 | 0.05 | 0.09 | 0.18 | 0.25 |
| C28:6n3 | 0.06 | 0.1 | 0.18 | 0.36 | 0.49 |
| C28:7n3 | 0.08 | 0.15 | 0.25 | 0.52 | 0.73 |
| C28:8n3 | 0.89 | 1.58 | 2.77 | 5.74 | 7.97 |
| Total C18-C22 n3 | 70.95 | 82.63 | 79.44 | 71.87 | 65.44 |
| Sum VLCn3 | 4 | 6.43 | 9.97 | 17.56 | 23.7 |
| Total n3 incl VLC | 74.95 | 89.06 | 89.41 | 89.43 | 89.14 |

Example 6

2040 g of the residue from the final commercial scale distillation of an ethylated sardine and mackerel oil utilized to produce an omega-3-acid concentrate containing about 36% EPA and about 26% DHA was hydrolyzed by heating for 80° C. for 1 hours in 4.0 kg of 90% ethanol containing 367 g sodium hydroxide. The composition of this residue starting material is presented in Table 5. After cooling to 20° C., removal of some precipitate by filtration and acidification, 1584 g of an oily product was isolated. The composition of this Oily Product is also presented in Table 5.

1518 g of this oily product was passed through a laboratory short path distillation still (VTA, model VKL-70-4-SKR-T) several times at 130-140° C. and 0.003 mbar, at a flow of 5.5 ml/min., to remove short-chain fatty acids in the distillate, while the VLCPUFA was concentrated in the residue. The residue fraction was then distilled at 170° C. and 0.003 mbar, at a flow of 5.5 ml/min to take the VLCPUFA in the distillate fraction, leaving heavy components in the residue.

The double distilled oil ("Distillate") (50 gram) had a composition given in Table 5. The product contained 9.54% of identified VLCPUFAs, and a total of 87.68% of omega-3 acids.

The skilled person will realize that all these products may be further purified before use, for example by adsorption, extraction, distillation or chromatographic procedures.

TABLE 5

| Fatty acid | Starting material | Oily Product | Distillate |
|---|---|---|---|
| 20:4n3 | 0 | 0.83 | 0 |
| 20:5n3 (EPA) | 16.77 | 20.83 | 0.65 |

TABLE 5-continued

| Fatty acid | Starting material | Oily Product | Distillate |
|---|---|---|---|
| 21:5n3 | 1.65 | 2.02 | 0.79 |
| 22:5n3 (n3DPA) | 6.81 | 7.96 | 12.14 |
| 22:6n3 (DHA) | 39.91 | 48.67 | 64.56 |
| 24:5n3 | 0.22 | 0.21 | 1.36 |
| 24:6n3 | 0.19 | 0.32 | 0.24 |
| 26:4n3 | 0.05 | 0.04 | 0.26 |
| 26:5n3 | 0.11 | 0.09 | 0.54 |
| 26:6n3 | 0.17 | 0.20 | 1.22 |
| 26:7n3 | nq | nq | 0.37 |
| 28:5n3 | 0 | 0.05 | 0.25 |
| 28:6:n3 | 0 | 0 | |
| 28:7n3 | 1.13 | 1.38 | 0.19 |
| 28:8n3 | 0 | 0 | 5.11 |
| 30:5n3 | 0 | 0 | |
| 30:6n3 | 0 | 0 | |
| Sum VLCn3 | 1.9 | 2.29 | 9.54 |
| Sum n3 | 68.7 | 84.38 | 87.68 |

Results in GC area percent. nq = not quantified

Example 7

The content of the ethyl esters of short chain fatty acids of the mackerel oil described in column 2 of Table 6 was reduced by a two-step distillation procedure, using short path distillation (VTA, model VK83-6-SKR-G with degasser). A flow of 6 kg/h and a vacuum of 0.02 mbar. The temperature in the first column was 125° C., while the temperature in the second column was 139° C. This procedure gave a distillate 1 of 55.4%. A distillate 2 of 34.5% and a residue 2 of 10.1% was obtained. The composition of ethyl esters of this residue 2 is given in column 3 of Table 6 below.

1500 g of the residue 2 from above was hydrolyzed by heating at 80° C. for 1 hour in 4.5 L ethanol (96%) containing 168 g Lithium hydroxide monohydrate and 70.5 g potassium hydroxide. After cooling to 20° C., removal of precipitate by filtration and acidification using an excess of citric acid in water, 812 g of an oily product was isolated. The composition of this oily product is detailed in column 4 of Table 6.

775 g of this oily product was passed through a laboratory short path distillation still (VTA, model VKL-70-4-SKR-T) several times at 130-140° C. and 0.003 mbar, at a flow of 5.5 ml/min., to remove short-chain fatty acids in the distillate, while the VLCPUFA was concentrated in the residue. The Residue fraction was then distilled at 170° C. and 0.003 mbar, at a flow of 5.5 ml/min to take the VLCPUFA in the distillate fraction, leaving heavy components in the residue. Such Residue Fraction has the fatty acid profile given in column 5 of Table 6.

The double distilled oil (Distillate) (150 g) had the composition given in column 6 of Table 6. The product contained 7.41% of identified VLCPUFAs, and a total of 70.99% of omega-3 acids.

This experiment shows that it is possible to distill of the VLCPUFA in a short path distillator, this is an important step for removing heavy components from the oil and improve the purity and color of the oil.

The skilled person will realize that all these products may be further purified before use, for example by adsorption, extraction, distillation or chromatographic procedures.

TABLE 6

| | | Column | | | |
|---|---|---|---|---|---|
| 1 Fatty acid | 2 Starting material (Mackerel oil) | 3 Product after EE distillation | 4 Oily Product | 5 Residue Fraction | 6 Distillate |
| 20:4n3 | 1.1 | 0.68 | 1.08 | 0.29 | 0.36 |
| 20:5n3 (EPA) | 8.84 | 4.69 | 7.82 | 1.52 | 1.99 |
| 21:5n3 | 0.48 | 0.51 | 0.85 | 0.58 | 0.74 |
| 22:5n3 (n3DPA) | 1.37 | 2.74 | 4.45 | 5.69 | 6.62 |
| 22:6n3 (DHA) | 11.41 | 20.24 | 33.84 | 46.89 | 53.87 |
| 24:5n3 | nq | 0.73 | 1.22 | 3.2 | 2.77 |
| 24:6n3 | nq | 0.24 | 0.11 | 0.47 | 0.41 |
| 26:4n3 | 0.03 | 0.25 | 0.20 | 0.56 | 0.36 |
| 26:5n3 | nq | 0.10 | 0.10 | 0.28 | 0.14 |
| 26:6n3 | 0.02 | 0.13 | 0.20 | 0.57 | 0.34 |
| 26:7n3 | nq | 0.11 | 0.07 | 0.22 | 0.19 |
| 28:5n3 | 0.03 | 0.25 | 0.12 | 1.06 | 0.56 |
| 28:6:n3 | nq | nq | ng | nq | nq |
| 28:7n3 | nq | nq | nq | nq | nq |
| 28:8n3 | 0.08 | 0.68 | 1.16 | 4.11 | 1.39 |
| 30:5n3 | 0.03 | 0.31 | 0.08 | 0.80 | 0.43 |
| 30:6n3 | 0.05 | 0.47 | 0.27 | 1.82 | 0.82 |
| Sum VLCn3 | 0.24 | 3.27 | 3.53 | 13.09 | 7.41 |
| Sum n3 | 23.44 | 32.13 | 51.57 | 68.06 | 70.99 |

Results in GC area percent. nq = not quantified

Example 8

The content of the ethyl esters of short chain fatty acids of the mackerel oil (Starting Material) described in column 2 of Table 7 was reduced by a two-step distillation procedure, using short path distillation (VTA, model VK83-6-SKR-G with degasser) with a flow of 6 kg/h and a vacuum of 0.02 mbar. The temperature in the first column was 125° C., while the temperature in the second column was 139° C. This procedure gave a distillate 1 of 55.4%, a distillate 2 of 34.5% and a residue 2 of 10.1% was obtained. The composition of ethyl esters of this residue 2 is given in column 3 of Table 7 below.

1000 g of the residue 2 from above was hydrolyzed by heating for 80° C. for 1 hour in 3.0 kg ethanol (96%) containing 140 g sodium hydroxide. After cooling to 20° C., removal of precipitate by filtration and acidification using an excess of citric acid, 310 g of an oily product was isolated. The oily product had the composition listed in column 4 of Table 7.

300 g of this product was passed through a laboratory short path distillation still (VTA, model VKL-70-4-SKR-T) several times at 130-134° C. and 0.003 mbar, at a flow of 5.5 ml/min., to remove short-chain fatty acids in the distillate, while the VLCPUFA was concentrated in the Residue Fraction. The composition of this Residue Fraction is presented in column 5 of Table 7. The Residue Fraction was then distilled at 170° C. and 0.003 mbar, at a flow of 5.5 ml/min to take the VLCPUFA in the distillate fraction, leaving heavy components in the residue.

The double distilled oil (Distillate) (112 grams) had a composition given in column 6 of Table 7. The product contained 7.41% of identified VLCPUFAs, and a total of 70.99% of omega-3 acids.

This experiment shows that it is possible to distill the VLCPUFA in a short path distillatory; this is an important step for removing heavy components from the oil and improve the color of the oil expressively.

The skilled person will realize that all these products may be further purified before use, for example by adsorption, extraction, distillation or chromatographic procedures.

TABLE 7

| | Column | | | | |
|---|---|---|---|---|---|
| 1 Fatty acid | 2 Starting material (Mackerel oil) | 3 Product after EE distillation | 4 Product after precipitation | 5 Residue Fraction | 6 Distillate |
| 20:4n3 | 1.1 | 0.68 | 1.33 | 0.35 | 0.36 |
| 20:5n3 (EPA) | 8.84 | 4.69 | 10.64 | 2.03 | 2.09 |
| 21:5n3 | 0.48 | 0.51 | 1.14 | 0.75 | 0.78 |
| 22:5n3 (n3DPA) | 1.37 | 2.74 | 5.16 | 6.36 | 6.63 |
| 22:6n3 (DHA) | 11.41 | 20.24 | 43.99 | 50.63 | 53.65 |
| 24:5n3 | nq | 0.73 | 1.53 | 3.31 | 3.18 |
| 24:6n3 | nq | 0.24 | 0.10 | 0.12 | 0.07 |
| 26:4n3 | 0.03 | 0.25 | 0.12 | 0.32 | 0.22 |
| 26:5n3 | nq | 0.10 | 0.07 | 0.18 | 0.13 |
| 26:6n3 | 0.02 | 0.13 | 0.22 | 0.53 | 0.41 |
| 26:7n3 | nq | 0.11 | 0.09 | 0.2 | 0.05 |
| 28:5n3 | 0.03 | 0.25 | 0.31 | 0.93 | 0.42 |
| 28:6:n3 | nq | nq | nq | nq | nq |
| 28:7n3 | nq | nq | nq | nq | nq |
| 28:8n3 | 0.08 | 0.68 | 1.52 | 4.27 | 1.90 |
| 30:5n3 | 0.03 | 0.31 | 0.07 | 0.31 | 0.08 |
| 30:6n3 | 0.05 | 0.47 | 0.32 | 1.11 | 0.28 |
| Sum VLCn3 | 0.24 | 3.27 | 4.35 | 11.28 | 6.74 |
| Sum n3 | 23.44 | 32.13 | 66.61 | 71.4 | 70.25 |

Results in GC area percent. nq = not quantified

Example 9

40.2 g free fatty acids (FFA) obtained from hydrolysis of the residue from a final commercial scale distillation of an ethylated sardine and mackerel oil utilized to produce an omega-3-acid concentrate containing about 46% EPA and about 13% DHA (the starting material) was stirred together with 120 g urea in 200 ml 96% ethanol at 80° C. for 1.5 h. The mixture was left over night in a batch containing a mixture of water and ice. After filtering to obtain the first filtration urea adducts or UA1 the filtrate was evaporated at reduced pressure to around half of the original volume. The resulting mixture was stored at around 4° C. overnight. Precipitated material (the second filtration urea adducts or UA2) was removed by filtration.

The isolated urea adducts (UA1 and UA2) were acidified with 4N HCl and extracted with hexane/water. The hexane was removed by evaporation at reduced pressure. In this way 10.3 g free fatty acids were isolated from the urea adducts from the first filtration UA1; and 1.51 g free fatty acids were isolated from the urea adducts from the second filtration UA2.

After work-up of the final filtrate by addition of an equal amount of water, acidification with hydrochloric acid, extraction with hexane and removal of the hexane solvent, 14.7 g non urea adduct (NUA) FFAs were isolated.

In Table 8 it is seen that among the VLCn3s, for each chain length the NUA product contains increased concentrations of the VLCn3 with the highest number of double bonds, while there are reduced concentrations of the VLCn3s with the lowest number of double bonds. For chain length 24 this is illustrated by C24:6n3 being up-concentrated in the NUA, while the concentration is reduced in UA1. Opposite to this, the fatty acid C24:5n3 is up-concentrated in UA1 and UA2, while this fatty acid is substantially removed from the NUA product. C24:5n3 and C24:6n3 differ only in that the latter contains one more double bond than the former. This possibility of a substantial physical separation of two very long polyunsaturated fatty acids with highly related structures is highly surprising.

Similarly, Table 8 shows that C26:4n3 and C28:4n3 were not found in the NUA product, while C28:8n3 is up-concentrated in the NUA.

TABLE 8

| Fatty acid | Starting Material | UA1 | UA2 | NUA Product |
|---|---|---|---|---|
| C24:5n3 RT35,19 | 1.16 | 2.03 | 2.25 | 0.18 |
| C24:6n3 RT35.81 | 1.09 | 0.66 | 1.1 | 1.44 |
| C26:4n3 RT40.42 | 0.07 | 0.14 | | |
| C26:5n3 RT41.20 | 0.19 | 0.42 | 0.12 | |
| C26:6n3 RT42.12 | 0.14 | 0.16 | 0.25 | 0.11 |
| C26:7n3 RT43.11 | 0.05 | 0.07 | 0.1 | 0.05 |
| C28:4n3 RT50.73 | 0.05 | 0.51 | 0.03 | |
| C28:5n3 RT51.15 | 0.22 | 0.01 | 0.03 | 0.05 |
| C28:6n3 RT52.00 | 0.06 | 0.1 | 0.12 | 0.01 |
| C28:7n3 RT53.64 | 0.08 | 0.12 | 0.18 | 0.03 |
| C28:8n3 RT55.69 | 0.89 | 0.39 | 0.82 | 1.41 |
| Total C18-C22 n3 | 70.95 | 41.13 | 83.96 | 90.94 |
| Sum VLCn3 | 4 | 4.73 | 5 | 3.28 |
| Total n3 incl. VLC | 74.95 | 45.86 | 88.96 | 94.22 |

Example 10

In each of three separate experiments 40 g the free fatty acid starting material employed in Example 9 was stirred in 200 ml 96% and 1.5, 2.0 and 3.0 weight parts of urea at 80° C. for 1.5 h.

The NUC fractions were isolated in the same way as in Example 9 above. The results from these experiments are presented in Table 9. From these results it is observed that there is no increase in the total VLCn3 concentrations in the NUC products. This means that for all experiments the urea adducts contain higher concentrations of VLCPUFAs than the starting FFA composition.

As above, it is surprisingly observed that urea fractionation can be used as a tool in order to separate VLCPUFAs with the same chain length: C24:5n3 is separated from C24:6n3 and C28:8n3 is separated from C28n3-acids with a lower degree of unsaturation.

Thus this method results in a relative separation of fatty acids within each group of VLCPUFAs with identical chain length. An example: from a mixture of C28:4n3, C28:5n3, C28:6n3, C28:7n3 and C28:8n3 can the fatty acids with the lowest number of double bonds be step-wise removed as urea adducts, while the fatty acids with the highest degree of unsaturation, especially C28:8n3, remain in the non-adduct fraction.

Thus it appears that urea fractionation surprisingly may be utilized as a relatively low-cost alternative to the manufacture of—for example—substantially pure C28:8n3 from a mixture of C28 omega-3 acids.

TABLE 9

| Fatty acid | Starting Material | 1.5 parts of urea | 2 p of urea | 3 p of urea |
|---|---|---|---|---|
| C24:5n3 RT35.19 | 1.16 | 0.24 | 0.23 | 0.63 |
| C24:6n3 RT35.81 | 1.09 | 1.46 | 1.45 | 1.4 |
| C26:4n3 RT40.42 | 0.07 | | | |
| C26:5n3 RT41.20 | 0.19 | | 0.01 | 0.05 |
| C26:6n3 RT42.12 | 0.14 | 0.11 | 0.09 | 0.12 |

TABLE 9-continued

| Fatty acid | Starting Material | 1.5 parts of urea | 2 p of urea | 3 p of urea |
|---|---|---|---|---|
| C26:7n3 RT43.11 | 0.05 | 0.04 | 0.04 | 0.05 |
| C28:4n3 RT50.73 | 0.05 | | | 0.02 |
| C28:5n3 RT51.15 | 0.22 | 0.06 | 0.05 | 0.05 |
| C28:6n3 RT52.00 | 0.06 | 0.02 | 0.01 | 0.04 |
| C28:7n3 RT53.64 | 0.08 | 0.03 | 0.02 | 0.05 |
| C28:8n3 RT55.69 | 0.89 | 1.42 | 1.42 | 1.33 |
| Total C18-C22 n3 | 70.95 | 89.63 | 90.78 | 89.63 |
| Sum VLCn3 | 4.0 | 3.38 | 3.32 | 3.79 |
| Total n3 incl. VLC | 74.95 | 93.01 | 94.1 | 93.42 |

What is claimed is:

1. A method for obtaining an enriched nutraceutical or pharmaceutical composition comprising at least 5% by weight of a mixture of at least two polyunsaturated fatty acids having a chain length of more than 22 carbon atoms and at least 5% by weight of $C_{20}$-$C_{22}$ polyunsaturated fatty acids from an oil composition isolated from fish oil, squid oil, krill oil or algal oil, the method comprising the steps of:

A) hydrolyzing an oil composition isolated from fish oil, squid oil, krill oil or algal oil and comprising (i) polyunsaturated fatty acids having a chain length of more than 22 carbon atoms and (ii) $C_{20}$-$C_{22}$ polyunsaturated fatty acids with a base in the presence of an organic solvent selected from the group consisting of $C_1$-$C_5$ alcohols and ketones of the formula $R^1(C=O)R^2$ wherein $R^1$ and $R^2$ are each independently $C_1$-$C_5$ alkyl, and water to form a composition comprising free fatty acid salts of polyunsaturated fatty acids having a chain length of more than 22 carbon atoms;

B) reacting the composition comprising the free fatty acid salts of the polyunsaturated fatty acids having a chain length of more than 22 carbon atoms formed in step A) with an acid to form a composition comprising polyunsaturated free fatty acids having a chain length of more than 22 carbon atoms; and C) concentrating the polyunsaturated fatty acids having a chain length of more than 22 carbon atoms present in the composition comprising polyunsaturated free fatty acids having a chain length of more than 22 carbon atoms to produce the enriched nutraceutical or pharmaceutical composition comprising at least 5% by weight of a mixture of at least two polyunsaturated fatty acids having a chain length of more than 22 carbon atoms and at least 5% by weight of $C_{20}$-$C_{22}$ polyunsaturated fatty acids.

2. A method for obtaining an enriched nutraceutical or pharmaceutical composition comprising at least 5% by weight of a mixture of at least two polyunsaturated fatty acids having a chain length of more than 22 carbon atoms and at least 5% by weight of $C_{20}$-$C_{22}$ polyunsaturated fatty acids from an oil composition isolated from fish oil, squid oil, krill oil or algal oil, the method comprising the steps of:

a) hydrolyzing an oil composition isolated from fish oil, squid oil, krill oil or algal oil and comprising (i) polyunsaturated fatty acids having a chain length of more than 22 carbon atoms and (ii) $C_{20}$-$C_{22}$ polyunsaturated fatty acids with a base in the presence of an organic solvent selected from the group consisting of $C_1$-$C_5$ alcohols and ketones of the formula $R^1(C=O)R^2$ wherein $R^1$ and $R^2$ are each independently $C_1$-$C_5$ alkyl, and water to form a composition comprising free fatty acid salts of polyunsaturated fatty acids having a chain length of more than 22 carbon atoms;

b) subjecting the composition formed in step a) to conditions such that (i) a precipitate and (ii) a filtrate comprising free fatty acid salts of polyunsaturated fatty acids having a chain length of more than 22 carbon atoms are formed;

c) removing the precipitate to obtain a filtrate comprising free fatty acid salts of polyunsaturated fatty acids having a chain length of more than 22 carbon atoms;

d) reacting the filtrate comprising free fatty acid salts of polyunsaturated fatty acids having a chain length of more than 22 carbon atoms with an acid to form a composition comprising polyunsaturated free fatty acids having a chain length of more than 22 carbon atoms; and e) concentrating the polyunsaturated fatty acids having a chain length of more than 22 carbon atoms present in the composition comprising polyunsaturated free fatty acids having a chain length of more than 22 carbon atoms to produce the enriched nutraceutical or pharmaceutical composition comprising at least 5% by weight of a mixture of polyunsaturated fatty acids having a chain length of more than 22 carbon atoms and at least 5% by weight of $C_{20}$-$C_{22}$ polyunsaturated fatty acids.

3. The method of claim 1, wherein the oil composition is isolated from fish oil.

4. The method of claim 1, further comprising removing shorter chain fatty acids from the oil composition prior to hydrolysis in step A).

5. The method of claim 4, wherein the oil composition hydrolyzed in step A) is a residue of a distillation or of an extraction used to produce a fish or squid oil concentrate of EPA and/or DHA.

6. The method of claim 1, further comprising removing shorter chain fatty acids from the composition comprising free fatty acid salts of polyunsaturated fatty acids having a chain length of more than 22 carbon atoms, or removing shorter chain fatty acids from the composition comprising polyunsaturated free fatty acids having a chain length of more than 22 carbon atoms after step A).

7. The method of claim 1, wherein the composition comprising free fatty acid salts of polyunsaturated fatty acids having a chain length of more than 22 carbon atoms produced in step A) is treated with a lipophilic solvent to reduce the amount of unsaponifiable material present.

8. The method of claim 2, wherein the filtrate comprising free fatty acid salts of polyunsaturated fatty acids having a chain length of more than 22 carbon atoms produced in step c) is treated with a lipophilic solvent to reduce the amount of unsaponifiable material present.

9. The method of claim 1, wherein the base added in step A) is at least one base selected from the group consisting of potassium hydroxide, sodium hydroxide, lithium hydroxide, potassium carbonate, sodium carbonate, lithium carbonate, potassium bicarbonate, sodium bicarbonate and lithium bicarbonate.

10. The method of claim 2, wherein the base added in step a) is lithium hydroxide, lithium carbonate or lithium bicarbonate, and wherein lithium salts of monounsaturated fatty acids having a chain length of more than 22 carbon atoms are recovered from the precipitate removed in step c).

11. The method of claim 1, wherein the polyunsaturated free fatty acids having a chain length of more than 22 carbon atoms are concentrated in step C) using distillation, chromatography, extraction or enzymatic processing.

12. The method of claim 11, wherein the polyunsaturated free fatty acids having a chain length of more than 22 carbon atoms are converted to alkyl esters before being concentrated.

13. The method of claim 1, wherein polyunsaturated fatty acids having a chain length of more than 22 carbon atoms and having identical chain lengths but different degrees of unsaturation which are present in the enriched composition produced in step C) are separated employing urea fractionation.

14. The method of claim 1, wherein the enriched nutraceutical or pharmaceutical composition produced in step C) comprises at least 10% by weight of a mixture of polyunsaturated fatty acids having a chain length of more than 22 carbon atoms.

15. An enriched composition comprising:
- at least 5% by weight of a mixture of at least two polyunsaturated fatty acids having a chain length of more than 22 carbon atoms, and
- at least 5% by weight of $C_{20}$-$C_{22}$ polyunsaturated fatty acids,
- wherein the polyunsaturated fatty acids are isolated from fish oil, and the composition is a nutraceutical or pharmaceutical composition.

16. The composition of claim 15, wherein the at least two polyunsaturated fatty acids having a chain length of more than 22 carbon atoms are in the form of ethyl esters or triglycerides.

17. The composition of claim 15, comprising at least 10% by weight of the mixture of the at least two polyunsaturated fatty acids having a chain length of more than 22 carbon atoms.

18. The composition of claim 15, wherein the mixture of the at least two polyunsaturated fatty acids having a chain length of more than 22 carbon atoms comprises at least 5% by weight of C28:7 and/or C28:8 polyunsaturated fatty acids.

19. The composition of claim 15, comprising at least 25% by weight of the $C_{20}$-$C_{22}$ polyunsaturated fatty acids.

20. The composition of claim 15, comprising at least 5% by weight of Omega-3 DPA.

21. The composition of claim 15, wherein the polyunsaturated fatty acids having a chain length of more than 22 carbon atoms and the $C_{20}$-$C_{22}$ polyunsaturated fatty acids are in the form of ethyl esters or triglycerides.

22. The composition of claim 15, wherein the at least two polyunsaturated fatty acids having a chain length of more than 22 carbon atoms are selected from the group consisting of C24:4, C24:5, C24:6, C26:4, C26:5, C26:6, C26:7, C28:4, C28:5, C28:6, C28:7, C28:8, C30:5 and C30:6 fatty acids.

* * * * *